(12) United States Patent
Ng et al.

(10) Patent No.: US 6,335,319 B1
(45) Date of Patent: *Jan. 1, 2002

(54) TREATMENT OF OBESITY

(75) Inventors: Frank Man-Woon Ng, Kew; Siria Helen Anna Natera, Mount Waverly; Woei-Jia Jiang, Clayton, all of (AU)

(73) Assignee: Metabolic Pharmaceuticals, Inc., Toorak (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/245,712

(22) Filed: Feb. 8, 1999

Related U.S. Application Data (63) Continuation-in-part of application No. 08/340,389, filed on Nov. 15, 1994, now Pat. No. 5,869,452.

(51) Int. Cl.[7] ............................ A61K 38/03; C07K 7/00
(52) U.S. Cl. ............................ 514/14; 514/12; 514/13; 530/324; 530/325; 530/326
(58) Field of Search ............... 514/12–14; 530/324–326

(56) References Cited

U.S. PATENT DOCUMENTS

| | | | | |
|---|---|---|---|---|
| 4,670,393 A | * | 6/1987 | Seeburg | 435/240 |
| 4,863,901 A | | 9/1989 | Wilmore | 514/12 |
| 4,871,835 A | | 10/1989 | Aviv et al. | 530/399 |
| 5,597,797 A | | 1/1997 | Clark | 514/12 |
| 5,869,452 A | * | 2/1999 | Ng et al. | 514/4 |

FOREIGN PATENT DOCUMENTS

| WO | 90/04788 | * | 5/1990 |
| WO | 92/09690 | * | 6/1992 |

OTHER PUBLICATIONS

S. H. A. Natera et al., "Reduction of Cumulative Body Weight Gain and Adipose Tissue Mass In Obese Mice: Response To Chronic Treatment With Synthetic HGH 177–191 Peptide", Biochemistry and Molecular Biology International, vol. 33, No. 5, Aug. 1994, pp. 1011–1021.

Wu et al. "Antilipogenic Action Of Synthetic C–Terminal Sequence 177–191 Of Human Growth Hormone," *Biochemistry and Molecular Biology International* Vol. 30:1 187–96 (May 1993).

Newman et al., Biochim. et Biophys. Acta. 544 (1978), 234–244.

Campbell et al., Proc. Soc. Exper. Biol. Med., vol. 193, No. 4, (4/90) pp. 269–273.

Ma et al., Biochim. et Biophys. Acta. 716 (1982), pp. 400–409.

Nishikawa et al., Pro. Engin, vol. 3, No. 1, pp. 49–53 (1989).

Remington's Pharmaceutical Sciences, 18th Ed. 1990, 99. 1633–1636, 1676–1679.

J. Marx. Science, vol. 266, No. 2. 12'/94.

T. Rink, Nature, vol. 372:1, pp. 406–407, (12/95).

Wijaya et al., Biochemistry and Molecular Biology International, vol. 31, No. 3 Nov. 1993.

Natera et al., Biochem and Molec. Bio. International, vol. 33, No. 5, Aug. 1994.

* cited by examiner

*Primary Examiner*—Bennett Celsa
(74) *Attorney, Agent, or Firm*—Foley & Lardner (57) ABSTRACT

A method for the treatment of obesity in an animal such as a human, comprises administering to the animal an effective amount of a peptide which comprises the carboxyl-terminal sequence of a growth hormone, particularly the carboxyl-terminal sequence of human growth hormone containing amine acid residues 177–191. A pharmaceutical composition for use in the treatment of obesity is also disclosed.

7 Claims, 2 Drawing Sheets

TREATMENT OF OBESITY

CROSS-REFERENCE TO RELATED APPLICATIONS

This application is a continuation-in-part of application Ser. No. 08/340,389, filed Nov. 15, 1994 now U.S. Pat No. 5,869,452.

FIELD OF THE INVENTION

This invention relates to the treatment of obesity in animals. In particular, the invention relates to the treatment of obesity in humans, although it is to be understood that the present invention also extends to the treatment of obesity in non-human mammals, for example, for the improvement of meat qualities in farm animals used in food production.

BACKGROUND OF THE INVENTION.

The critical role of human growth hormone (hGH) in postnatal growth in humans is well recognised. Less obvious is the impact of this hormone on the regulation of lipid and carbohydrate metabolism, due to lack of detailed molecular studies.

It is well documented that the predominant form of hGH is a globular protein with a molecular weight of 22,000 daltons (22-KD) and consists of 191 amino acid residues in a single-chain, folded by 2 disulphide bonds with a small loop at the carboxyl terminus between residues 182 and 189. Recent crystallographic studies also show that the hGH molecule contains four anti-parallel α-helices which are arranged in a left-twisted, tightly-packed helical bundle[1]. The concept that there are discrete functional domains within the hGH molecule responsible for specific metabolic actions of the hormone is generally accepted. The amino-terminus has, been identified as the functional domain responsible for the insulin-like actions of the hGH molecule[2,3].

Recombinant DNA technology opens the way to the large-scale commercial production of human growth hormone, and the recombinant hGH appears to have equivalent biological efficacies and pharmacokinetic properties[4,5]. Current supply of this multiple-functional hormone no longer restricts the types and numbers of experimental therapies in humans and animals. The use of hGH for treatment of short stature in children and adults is well-established[6]. Therapeutic effects of hGH in female infertility have also been reported[7,8]. Treatment of human obesity with hGH has been advocated because of its remarkable effects on body composition with lipid metabolism. However, the clinical applications of the intact hormone encounter a variety of problems. Evidence suggests that this multiple-functional hormone often simultaneously exerts in vivo, by various bioactive domains within the molecules, some adverse effects[10].

Regulation of lipid metabolism by GH was first described in 1959 by Raben & Hollenberg[11]. The acute increase of plasma free fatty acids after GH administration was the major evidence for this metabolic function of the hormone. The regulatory role of the hormone in lipid metabolism was subsequently supported by the body composition studies of GH-deficient and GH-treated humans[12,13] and pigs[14,15]. The findings of Gertner suggest that hGH is linked to adipose tissue distribution through a series of interactions known as the "GH-fat cycle"[16]. However, the molecular events transpiring to these biochemical and physiological changes remained largely unknown. The metabolic effects of GH on adipose and other tissues in vivo are variable and complex, apparently consisting of at least two components, an early insulin-like effect followed by a later more profound anti-insulin effect[17]. The results of the latter effect may include both a stimulation of lipolysis and an inhibition of lipogenesis. The anti-lipogenic effect of hGH has been substantiated with the demonstrations of the decrease of the expression of glucose transporter GLUT 4 in adipocytes[18], the inhibition of the activity of acetyl-CoA carboxylase in adipose tissues[19,20] and the reduction of glucose incorporation into lipid in both isolated cells and tissues[21,22].

In view of the multiple-functional effects of intact hGH and the problems encountered in clinical applications of the intact hormone, work leading to the present invention has been directed to investigating whether hGH derivatives could be synthesised that retain the desired bioactivities and lack the unwanted side effects. In this work, structure-function studies of hGH have been carried out to elucidate the molecular mechanism of the metabolic actions of this multiple-functional hormone.

SUMMARY OF THE INVENTION

The present invention concerns a method for treating obesity comprising administering an effective amount of a peptide wherein the amino acid sequence of the peptide comprises the carboxyl-terminal sequence of a growth hormone. The treatment may be administered to any animal, including humans. The peptide may comprise the carboxyl-terminal sequence of human growth hormone or the growth hormone of a non-human mammalian species.

In one embodiment of the invention, the peptide comprises the carboxyl-terminal sequence of human growth hormone containing amino acid residues 177–191. In other embodiments of the invention, the peptide comprises the carboxyl-terminal sequence of the growth hormone of a non-human mammalian species corresponding to amino acid residue 177–191 of human growth hormone.

In another aspect, the present invention also concerns a pharmaceutical composition for use in the treatment of obesity comprising an effective amount of a peptide wherein the amino acid sequence of the carboxyl-terminal sequence of a growth hormone, and one or more pharmaceutically acceptable carriers and/or diluents. The peptide may comprise the carboxyl-terminal sequence of human growth hormone or the growth hormone of a non-human mammalian species.

In one embodiment of this aspect of the invention, the peptide comprises the carboxyl-terminal sequence of human growth hormone containing amino acid residues 177–191. In other embodiments of this aspect of the invention, the peptide comprises the carboxyl-terminal sequence of the growth hormone of a non-human mammalian species corresponding to amino acid residues 177–191 of human growth hormone.

DESCRIPTION OF THE PREFERRED EMBODIMENTS

The structure-function studies of hGH with synthetic hormonal fragments have revealed that the carboxyl terminus of the hGH molecule appears to be the functional domain of the hormone for the regulation of lipid metabolism[20,23,24,25] and it has now been shown that a synthetic peptide having a sequence based in the carboxyl terminal region reduces body weight gain and adipose tissue mass in a laboratory obese animal model.

According to one aspect of the present invention, there is provided a method for the treatment of obesity in an animal, which comprises administering to the animal an effective amount of a peptide wherein the amino acid sequence of the peptide comprises the carboxyl-terminal sequence of a growth hormone, and wherein the peptide is not the intact, full length growth hormone.

Preferably, the animal is a human although the invention also extends to the treatment of non-human mammals. Preferably also, the peptide comprises the carboxyl-terminal sequence of human growth hormone containing amino acid residues 177–191 (SEQ ID NO: 1), hereinafter referred to as hGH 177–191. Alternatively, the peptide may comprise the carboxyl-terminal sequence of the growth hormone of other non-human mammalian species, such as bovine, porcine, ovine, equine, feline or canine growth hormone corresponding to the hGH 177–191 peptide.

As used throughout this specification, the term "obesity" is used to include both excess body weight and excess adipose tissue mass in the animal, and correspondingly the references to treatment of obesity include both reduction of body weight gain and reduction of adipose tissue mass of the obese animal.

As described above, the carboxyl-terminal sequence of a growth hormone include a bioactive lipid methabolic domain effective to reduce body weight gain and adipose tissue mass in an obese animal. Thus, the peptide comprising the carboxyl-terminal sequence of a growth hormone in accordance with the present invention has in vivo lipid metabolic active, particular in vivo antilipogenesis and lipolytic activity.

The expected outcome of any treatment of obesity is the reduction of body weight, body adipose tissue mass in particular. The reduction of body adipose tissue mass is directly regulated by two biochemical processes— lipogenesis (fat-production) and lipolysis (fat-reduction)— and it is generally understood that these biochemical processes are controlled by key metabolic enzymes, specifically the fat-reducing key enzyme (hormone-sensitive lipase) and the fat-producing key enzyme (acetyl CoA carboxylase).

It has been shown by the present inventors that hGH 177–191 is effective in stimulating the fat-reducing key enzyme, hormone-sensitive lipase, and in inhibiting the fat-producing key enzyme, acetyl CoA carboxylase. This is further supported by data showing that in the presence of hGH 177–191, fat utilisation is accelerated while fat production is reduced, as measured by metabolic end-products in vitro as well as in vivo. In addition, the mechanism of these molecular actions has been established as resulting from the activation of the production of the cellular second-messenger, diacylglycerol.

The peptides of the present invention have been observed to retain the antilipogenic and lipolytic properties of intact hGH, while not having its diabetogenic or somatogenic properties. Specifically, hGH 177–191 at 500 μg/kg/day by IP injection for 18 days was shown not to alter the insulin sensitivity of both Wistar and Sucker (fa/fa) rats, unlike intact hGH. Competition binding studies of hGH and hGH 177–191 in BaF3 cells expressing the hGH receptor show no apparent competition between hGH and hGH 177–191 for the hGH receptor, and the BaF3 proliferation assay shows no activity with hGH 177–191, confirming lack of somatogenic activity.

It will, of course, be appreciated that the present invention extends to the use of peptides having longer amino acid sequences than the particular sequence 177–191 of growth hormone, for example the sequence 172–191 of human growth hormone (SEQ ID NO: 2) or the corresponding sequence of growth hormone of other non-human mammalian species, however the present invention does not extend to the use of intact full-length human growth hormone or growth hormone of other animal species. By way of example only, the peptide may be an amino acid sequence comprising from 15 carboxyl-terminal residues up to one half or more of the full-length sequence of human or non-human mammalian growth hormone.

The concept of correspondence in amino acid sequences between species is well known in the biological sciences and is determined by aligning comparable sequences (including if necessary theoretical deletions) to match isofunctional or isostereo amino acids thereby maximising homology. Such alignment of corresponding sequences may be performed by visual inspection or with the use of computer algorithms for example those shown in Thompson et al.[35] The published corresponding sequences of the C-terminus region of the growth hormone of selected mammals are tabulated below[36], using standard single letter notation:

| GH Species Position | Sequence 170      180      190 | | | |
|---|---|---|---|---|
| human | FRKDMDKVETFLRIVQCR.SVEGSCGF | SEQ | ID | NO 3 |
| human variant | FRKDMDKVETFLRIVQCR.SVEGSCGF | SEQ | ID | NO 3 |
| human CS | FRKDMDKVETFLRMVQCR.SVEGSCGF | SEQ | ID | NO 4 |
| monkey, rhesus | FRKDMDKIETFLRIVQCR.SVEGSCGF | SEQ | ID | NO 5 |
| rat | FKKDLHKAETYLRVMKCRRFAESSCAF | SEQ | ID | NO 6 |
| mouse | FKKDLHKAETYLRVMKCRRFVESSCAF | SEQ | ID | NO 7 |
| hamster | FKKDLHKAETYLRVMKCRRFVESSCAF | SEQ | ID | NO 8 |
| whale, fin | FKKDLHKAETYLRVMKCRRFVESSCAF | SEQ | ID | NO 9 |
| whale, sei | FKKDLHKAETYLRVMKCRRFVESSCAF | SEQ | ID | NO 9 |
| fox, dog, cat | FKKDLHKAETYLRVMKCRRFVESSCAF | SEQ | ID | NO 10 |
| mink | FKKDLHKAETYLRVMKCRRFVESSCAF | SEQ | ID | NO 11 |
| cattle | FRKDLHKTETYLRVMKCRRFGEASCAF | SEQ | ID | NO 12 |
| sheep | FRKDLHKTETYLRVMKCRRFGEASCAF | SEQ | ID | NO 13 |
| goat | FRKDLHKTETYLRVMKCRRFGEASCAF | SEQ | ID | NO 14 |
| pig | FKKDLHKAETYLRVMKCRRFVESSCAF | SEQ | ID | NO 15 |
| alpaca | FKKDLHKAETYLRVMKCRRFVESSCAF | SEQ | ID | NO 16 |
| horse | FKKDLHKAETYLRVMKCRRFVESSCAF | SEQ | ID | NO 17 |
| elephant | FKKDLHKAETYLRVMKCRRFVESSCAF | SEQ | ID | NO 18 |
| ancestral mammal | FKKDLHKAETYLRVMKCRRFVESSCAF | SEQ | ID | NO 19 |

The present invention also extends to the use of peptides which are homologues, analogues, mutants, variants or derivatives of the native carboxyl-terminal sequences of human growth hormone or growth hormone of other animal species, and which are derived from natural or synthetic (including recombinant) sources, provided always that the resulting peptide retains the biological activity of the native carboxyl-terminal sequence described herein, namely the ability to reduce body weight gain and adipose tissue mass in an obese animal.

These homologues, analogues, mutants, variants or derivatives may be derived by insertion deletion or substitution of amino acids in, or chemical modification of, the native carboxyl-terminal sequence. Amino acid insertional derivatives include amino and/or carboxylic terminal fusions as well as intra-sequence insertions of single or multiple amino acids. Insertional amino acid sequence variants are those in which one or more amino acid residues are introduced into a predetermined site in the protein although random insertion is also possible with suitable screening of the resulting product. Deletional variants are characterised by the removal of one or more amino acids from the sequence. Substitutional amino acid variants are those in which at least one amino acid residue in the sequence has been replaced by another of the twenty primary protein amino acids, or by a non-protein amino acid. Chemical modifications of the native carboxyl-terminal sequence include the acetylation of the amino-terminus and/or amidation of the carboxyl-terminus and/or side chain cyclisation of the native carboxyl-terminal sequence.

The term "effective amount" as used herein means an amount of the peptide sufficient to attain the desired effect in the treatment of obesity in the animal, but not so large an amount as to cause serious side effects or adverse reactions.

In another aspect, the present invention provides the use of an effective amount of a peptide wherein the amino acid sequence of the peptide comprises the carboxyl-terminal sequence of a growth hormone as described above in the treatment of obesity in an animal or in the manufacture of a pharmaceutical composition for the treatment of obesity in an animal.

In yet another aspect, the present invention provides a pharmaceutical composition for use in the treatment of obesity in an animal, comprising an effective amount of a peptide wherein the amino acid sequence of the peptide comprises the carboxyl-terminal sequence of a growth hormone as described above, together with one or more pharmaceutically acceptable carriers and/or diluents.

The peptide which is the active ingredient of the pharmaceutical composition of this aspect of the invention exhibits advantageous therapeutic activity in the treatment of obesity in an animal when administered in an amount appropriate to the particular case. For example, from about 0.5 $\mu$g to about 20 mg per kilogram of body weight per day may be administered. Dosage regimens may be adjusted to provide the optimum prophylactic or therapeutic response. For example, one or more divided doses may be administered daily, weekly, monthly or in other suitable time intervals or the dose may be proportionally reduced as indicated by the exigencies of the clinical situation.

The active ingredient may be administered in any convenient manner such as by the oral, parenteral (including intraperitoneal, intravenous, subcutaneous, intramuscular and intramedullary injection), intranasal, intradermal or suppository routes or by implanting (eg using slow release molecules). For ease of administration, oral administration is preferred, however parenteral administration is also quite convenient. Depending on the route of administration, the active ingredient may be required to be coated in a material that protects said ingredient from the action of enzymes, acids and other natural conditions which may inactivate the said ingredient. For example, low lipophilicity of the ingredient may allow it to be destroyed in the gastrointestinal tract by enzymes capable of cleaving peptide bonds and in the stomach by acid hydrolysis. In order to administer the composition by other than parenteral administration, the active ingredient may be coated by, or administered with, a material to prevent its inactivation.

The active ingredient may also be administered in dispersions prepared in glycerol, liquid polyethylene glycols, and/or mixtures thereof and in oils. Under ordinary conditions of storage and use, these preparations will usually contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thiomorosal, and the like. In many cases, it will be preferable to include isotonic agents, for example, sugars or sodium chloride. Prolonged absorption of the injectable compositions can be brought about by, for example, the use in the compositions of agents delaying absorption.

Sterile injectable solutions are prepared by incorporating the active ingredient in the required amount in the appropriate solvent with various of the other ingredients enumerated above, as required, followed by filtered sterilisation. Generally, dispersions are prepared by incorporating the sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredient is suitably protected as described above, the composition may be orally administered, for example, with an inert diluent or with an assimilable edible carrier, or it may be enclosed in hard or soft shell gelatin capsule, or it may be compressed into tablets, or it may be incorporated directly with the food of the diet. For oral administration, the active ingredient may be incorporated with excipients and used in the form of ingestible tablets, buccal tablets, troches, capsules, elixirs, suspensions, syrups, wafers, and the like. Such compositions and preparations should contain at least 0.01% by weight and more preferably at least 0.1–1% by weight of active ingredient. The percentage of the compositions and preparations may, of course, be varied and may conveniently be between about 5 to about 80% of the weight of the unit. The amount of active ingredient in the pharmaceutical compositions is such that a suitable dosage will be obtained. Preferred compositions or preparations according to the present invention may, for example, be prepared so that an oral dosage unit form contains between about 0.5 pg and 200 mg and more preferably 10 $\mu$g and 20 mg of active ingredient.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active ingredient may be incorporated into sustained-release preparations and formulations.

As used herein, pharmaceutically acceptable carriers and diluents include any and all solvents, dispersion media, aqueous solutions, coatings, antibacterial and antifungal agents, isotonic and absorption delaying agents, and the like. The use of such media and agents for pharmaceutically active substances is well known in the art, and it is described, by way of example, in *Remington's Pharmaceutical Sciences*, 18th Edition, Mack Publishing Company, Pennsylvania, USA. Except insofar as any conventional media or agent is incompatible with the active ingredient, use thereof in the pharmaceutical compositions of the present invention is contemplated. Supplementary active ingredients can also be incorporated into the compositions.

It is especially advantageous to formulate compositions in dosage unit form for ease of administration and uniformity of dosage. Dosage unit form as used herein refers to physically discrete units suited as unitary dosages for the human subjects to be treated; each unit containing a predetermined quantity of active ingredient calculated to produce the desired therapeutic effect in association with the required pharmaceutical carrier and/or diluent. The specifications for the novel dosage unit forms of the invention are dictated by and directly dependent on (a) the unique characteristics of the active ingredient and the particular therapeutic effect to be achieved, and (b) the limitations inherent in the art of compounding such an active ingredient for the treatment of obesity.

Throughout this specification and claims which follow, unless the context requires otherwise, the word "comprise" or variations such as "comprises" or "comprising", will be understood to imply the inclusion of a stated integer or group of integers but not the exclusion of any other integer or group of integers.

Further details of the present invention will be apparent from the following Example and the accompanying drawings which are included by way of illustration, not by way of limitation, of this invention.

BRIEF DESCRIPTION OF THE DRAWINGS

In the drawings:

FIG. 3 shows the ex vivo effect on lipogenesis in adipose tissues of the C57BL6J (ob/ob) mice after 18-day treatment with hGH 177–191. The tissues were preincubated at 37° C. for 1 hr in Krebs-Ringer Bicarbonate buffer (pH 7.4) containing 1% defatted BSA and 1 mM glucose. After preincubation, tissues were transferred to fresh media containing [$^{14}$C]-glucose (0.05 μCi/μmol) for a further 90 min incubation. Data indicate the rate of $^{14}$C-lipid synthesis and are expressed as $^{14}$C-glucose incorporated into lipid (pmol/mg tissue/min). Values are mean ±SEM of 12 determinations from 6 animals of each group. The differences between the hGH 177–191 treated and saline control groups were statistically significant (*p<0.1, **p<0.05).

EXAMPLE

Materials and Methods

Animals and Treatments.

Twelve male and twelve female C57BL6J (ob/ob) mice aged 12–13 weeks were used in this study. The animals of the same sex were randomly divided into two groups, housed 6 per cage and maintained on a normal 12-hr light/dark cycle at a constant room temperature of 25° C. in the animal house of the Biochemistry Department, Monash University, Clayton, Australia. Animals were fed ad libitum on pre-determined quantity of mouse pellets (Clark King, Melbourne, Australia) and allowed free access to water at all times. The mice were given a daily intraperitoneal (i.p.) injection of 0.1 ml of either the hGH 177–191 peptide (200 μg/kg body weight) or equivalent volume of physiological saline (0.9% sodium chloride) for 18 days. The i.p. injection was administered with a 30G×½" (0.31×13 mm) needle on a 1-ml disposable tuberculin syringe, and the site of injection was the lower left quadrant of the abdomen of the animals.

Peptide Synthesis.

hGH 177–191,

Leu—Arg—Ile—Val—Gln—Cys—Arg—Ser—Val—Glu—Gly—Ser—Cys—Gly—Phe, (SEQ ID NO: 1), was prepared by manual solid-phase synthesis of Fmoc-strategy using DIC/HOBt activation. The coupling reactions were monitored by using the ninhydrin method[26]. Acetamidomethyl(Acm) group was used for the side-chain protective group of two Cys residues. After completion, the peptide was cleaved from the resin and side-chain protective groups, except Acm, were removed by using Reagent k[27]. Removal of two Acm groups and simultaneous formation of the disulfide bond between Cys182 and Cys189 of hGH 177–191 were performed using the silyl-sulfoxide method[28]. Alternatively, other methods for formation of direct disulfide bonds may be used. After purification on RP-HPLC, the oxidised hGH 177–191 peptide was characterised with Waters Pico Tag (PITC) system for amino acid analysis [Arg: 1.92 (2), Cys: not determined (2), Glu/Gln: 2.00 (2), Gly: 2.27 (2), Ile: 0.84 (1), Leu: 1.19 (1), Phe: 1.10 (1), Ser: 1.54 (2), Val: 1.84 (2)] and with fast atom bombardment-mass spectrometer (FAB-Mass) for molecular weight determination, $[M+H]^+ +1652.0$ (experimental) for 1651.9 (calculated).

Cumulative Weight Gain and Food Consumption.

Cumulative weight gain and food consumption were determined at 3-day intervals by the measurements of body weight and uneaten food remaining in the cages. The animals were placed in a covered chamber to minimise movement during the weighing procedure. The food consumption data were obtained by subtracting the amount of uneaten food remaining in the cages from the original provision.

Assays for Plasma Triglyceride and Total Cholesterol.

The animals were anaesthetised with sodium pentobarbitone (80 mg/kg body weight) 12 hr after the last dose of hGH 177–191. Blood samples were collected from the tail vein of anaesthetised animals 45 mins after the administration of anaesthetic. After being centrifuged at 2000×g for 5 minutes, plasma was removed from the samples and used for metabolite assays. Triglyceride and total cholesterol in plasma were measured by enzyme-spectrophotometric methods. The reagents are based on either a modified glycerol phosphate oxidase (GPO)-Trinder's type colour reaction or a cholesterol oxidase-4-aminoantipyrine method[30]. All assays were performed with the CentrifiChem System 400 (Union Carbide) containing an automated pipetter, a centrifugal analyser and a recording spectrophotometer. Seronorm Lipid (Nycomed Pharma Co., Oslo, Norway) was used as the calibrator.

Determination of Adipose Tissue Weight.

The procedure for the isolation and measurement of intact epididymal fat pads was established in previous studies of epididymal growth of GH-deficient (lit/lit) mice. In the present study, white adipose tissues, either whole epididymal or parametrical fat pads, were excised with the identical techniques as previously described[22] from the mice immediately after sacrifice. The tissues were washed in cold physiological saline, blotted and weighed. For ex vivo lipogenic assays, the portions of adipose tissues without blood vessels were used.

Assay for Lipogenic Activity.

The rate of the incorporation of exogenous $[^{14}C]$-glucose into total lipid in adipose tissue was measured as the index of lipogenic activity[25,31,32]. Adipose tissues were sliced into segments of approximately 200 mg each and then placed in Krebs-Ringer Bicarbonate (KRB) buffer (pH 7.4) containing 1% defatted BSA and 1 mM glucose and gassed with 95% $O_2$–5% $CO_2$ at 37° C. After 1 hr preincubation, the tissues were transferred to another 2 ml of fresh media containing $[^{14}C]$-glucose (final specific activity 0.05 $\mu Ci/\mu mol$) for a further 90 min incubation (conditions as above). Then the tissues were removed, washed thoroughly with KRB buffer and lipid was extracted with a chloroform/methanol mixture[33]. $^{14}C$ radioactivity was counted in a Wallac 1410 Liquid Scintillation Counter. The rates of total lipid synthesis are expressed as pmol $[^{14}C]$-glucose incorporated into lipid/mg tissue/min.

Statistical Analysis.

The Student's t-test was used to analyse the results. All data are expressed as the mean ±SEM. P values of <0.05 are accepted as statistically significant.

RESULTS

Figure 1A:
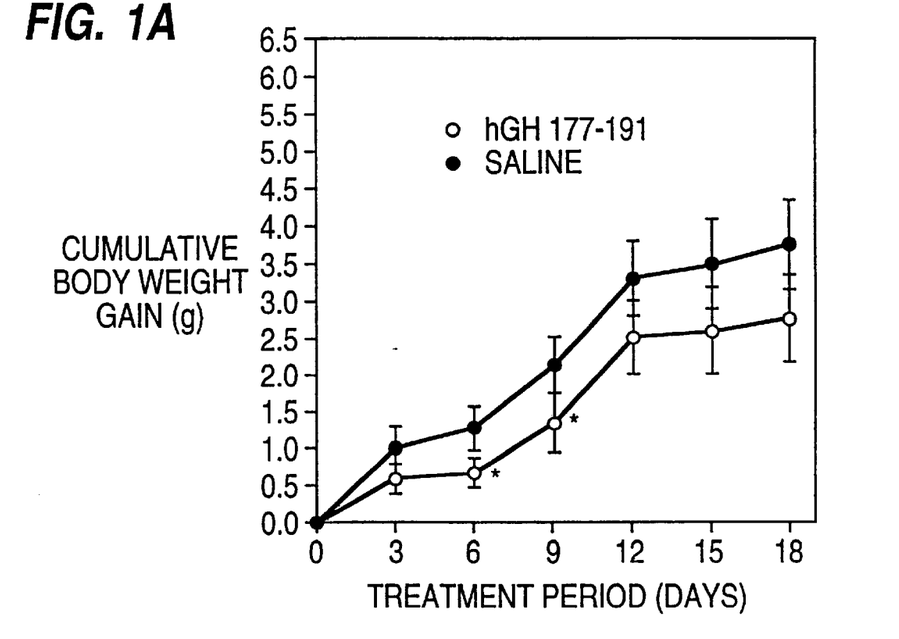
FIGS. 1A and 1B show the effects of hGH 177–191 peptide on cumulative weight gains in male (panel A) and female (panel B) C57BL6J (ob/ob) mice during an 18-day treatment period. Animals were given a daily intraperitoneal injection of 0.1 ml of either saline (●,▲) or synthetic hGH 177–91 peptide (200 μg/kg body weight) (○,▽). Body weight changes were determined at 3-day intervals and each point represents the mean ±SEM of 6 animals. The differences between the saline control and the hGH 177–191 treated groups were statistically analysed. *P<0.05 and **p<0.025 compared with corresponding controls.
Figure 1B:
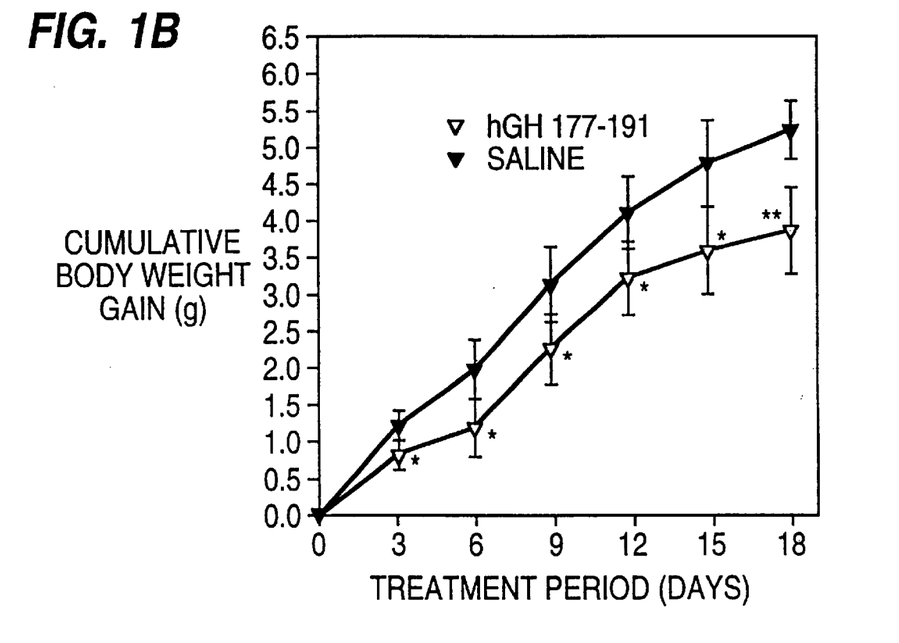
Figure 2:
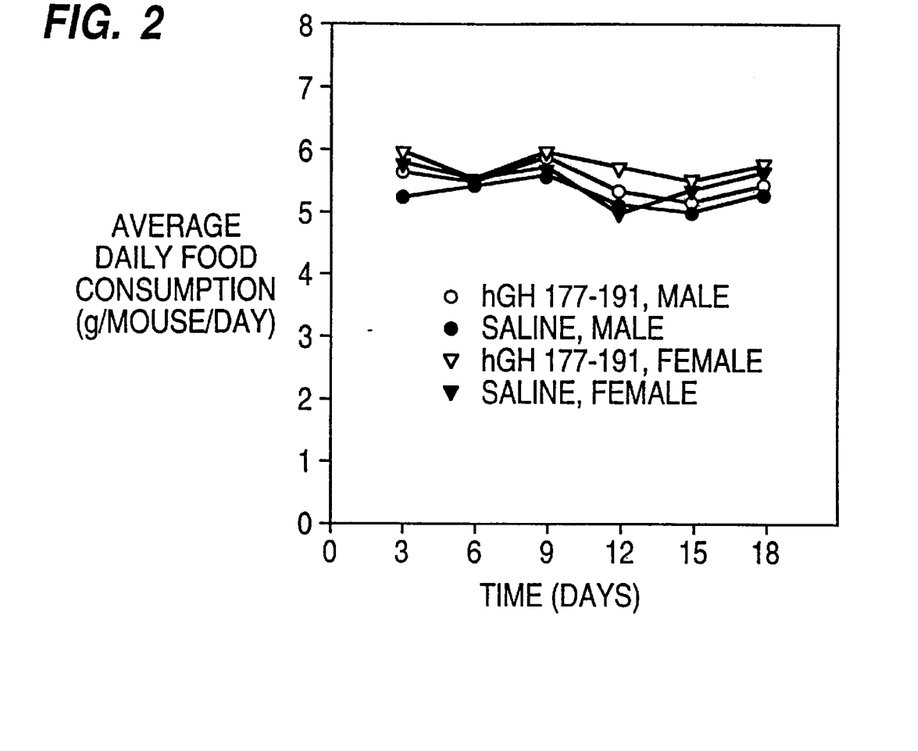
FIG. 2 shows the average daily food consumption (g/mouse/day) of C57BL6J (ob/ob) mice during an 18-day treatment period with hGH 177–191 peptide. The treatment for the four groups of animals was as described in FIGS. 1A and 1B. Food consumption of each group was determined at 3-day intervals and each point represents the mean±SEM of 6 animals. No significance between the groups was observed at all times.

The chronic treatment of the obese mice with the synthetic hGH 177–191 peptide was evaluated by the measurements of a number of parameters including cumulative body weight gain and daily food consumption. FIGS. 1A and 1B reveal that the control female animals appeared to have a larger mean cumulative body weight gain than their control male counterparts, similar to the observation previously reported by Ingalls et al.[34]. During the 18-day treatment period, a clear reduction of cumulative body weight gain was observed in the hGH 177–191-treated male as well as female animals when compared with the appropriate controls, indicating that the hGH fragment reduces the body weight gain in the obese mouse model. When the data were analysed and expressed as daily body weight gains, the treated male animals reduced their body weight gain from 0.22 ±0.03 to 0.16±0.04 g/day and the female animals from 0.30 ±0.02 to 0.22±g/day. The average daily body weight gains of the both male and female treated animals showed approximately 27% lower than those of the appropriate control groups. However, no significant difference in the average daily food consumption among the 4 groups was observed over the study period (FIG. 2). It was noted that the ratio of daily food consumption to daily body weight gain between the treated animals and control ones was different: 25±4 to 36±8 for the male mice and 18±2 to 27±6 for the female mice. These data clearly demonstrate that the chronic treatment with the hGH 177–191 peptide reduced the body weight gains without affecting food consumption.

Figure 3:
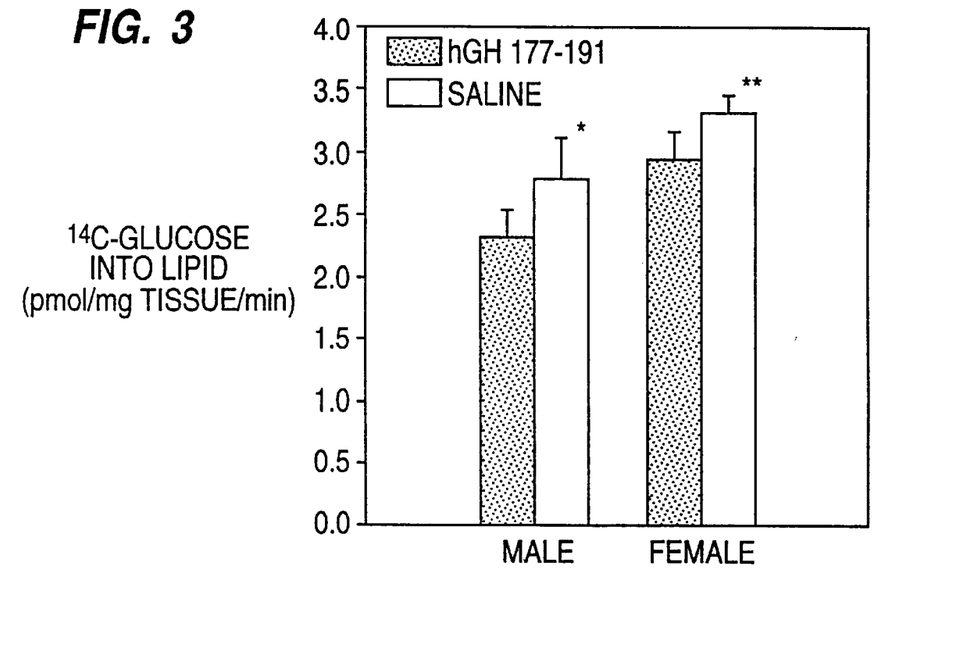

As indicated by the measurements of epididymal and parametrical fat pads, the treated mice significantly reduced their adipose tissue weights up to 20% in the males and 12% in the females as compared with the controls of the same sex (Table 1). Lipogenesis is subject to the supply of precursor metabolites such as glucose and acetate. The effect of hGH 177–191 on lipogenesis was therefore determined by measuring the incorporation of $[^{14}C]$-glucose into lipid in isolated adipose tissues. The hGH 177–191 peptide inhibited the lipogenesis from 2.80±0.33 to 2.33±0.21 pmol/mg tissue/min in the males and from 3.36±0.13 to 2.99±0.21 pmol/mg tissue/min in the females (FIG. 3). These results are consistent with the reductions in adipose tissue mass and cumulative body weight gain previously observed. Table 2 depicts the effect of the hGH 177–191 treatment on the profiles of circulating levels of triglyceride and cholesterol. The total cholesterol in plasma was significantly reduced from 4.44±0.56 to 3.52±0.39 mmol/l in the male animals, but the plasma levels of cholesterol in the treated female animals were only slightly lower than those of control ones. The responses to hGH 177–191 treatment between the male and female mice appeared to be different in this respect. On the other hand, hGH 177–191 did not influence the plasma levels of triglyceride in both sexes.

TABLE 1

Effect of synthetic hGH 177–191 peptide on body weight and adipose tissue mass of obese mice after 18–day chronic treatment. Animals were given a daily i.p. injection of either hGH 177–191 (200 $\mu$g/kg body weight) or equivalent volume of saline as control. All data represent the mean ± SEM of 6 animals (*p < 0.1; **p < 0.05).

|  | Male | | Female | |
| --- | --- | --- | --- | --- |
| Item | Control | Treated | Control | Treated |
| Initial body wt. (g) | 47.5 ± 3.1 | 48.6 ± 2.0 | 46.7 ± 3.6 | 48.2 ± 3.4 |
| Final body wt. (g) | 51.4 ± 3.0 | 51.5 ± 2.3 | 52.1 ± 3.2 | 52.2 ± 2.9 |

TABLE 1-continued

Effect of synthetic hGH 177–191 peptide on body weight and adipose tissue mass of obese mice after 18–day chronic treatment. Animals were given a daily i.p. injection of either hGH 177–191 (200 μg/kg body weight) or equivalent volume of saline as control. All data represent the mean ± SEM of 6 animals ($*p < 0.1$; $**p < 0.05$).

| | Male | | Female | |
|---|---|---|---|---|
| Item | Control | Treated | Control | Treated |
| Body wt. gain (g)[a] | 3.9 ± 0.6 | 2.9 ± 0.6* | 5.4 ± 0.4 | 4.0 ± 0.6** |
| Adipose tissue (g)[b] | 3.18 ± 0.43 | 2.52 ± 0.25** | 3.67 ± 0.54 | 3.26 ± 0.25** |

[a] The difference between the initial and final body weights were considered as body weight gain.
[b] The intact epididymal or parametrical fat pads were the representative adipose tissues.

TABLE 2

Effect of synthetic hGH 177–191 on plasma levels of triglyceride and total cholesterol in obese mice after 18-day chronic treatment. Blood samples were collected from the cut tips of the tails of the anaesthetised animals. Data represent the mean ± SEM of 6 animals ($*p < 0.05$).

| | Male | | Female | |
|---|---|---|---|---|
| Item | Control | Treated | Control | Treated |
| Triglyceride (mmol/l) | 0.63 ± 0.26 | 0.58 ± 0.16 | 0.41 ± 0.19 | 0.38 ± 0.11 |
| Cholesterol (mmol/l) | 4.44 ± 0.56 | 3.52 ± 0.39* | 3.01 ± 0.52 | 2.84 ± 0.29 |

REFERENCES

1. Ultsch, M. H., Somers, W., Kossiakof, A. A. and DeVos, A. M. (1994), *J. Mol. Biol.* 236: 286–299.
2. Ng, F. M., Bornstein, J., Welker, C., Zimmet, P. Z. and Taft, P. (1974). *Diabetes* 23: 943–949.
3. Frigeri, L. G., Teguh, C., Lind.N., Wolff, G .L. and Lewis, U. J. (1988). *Endocrinology* 122: 2940–2945.
4. Moore, W. V., Moore, K. C., McLachlan, C. G., Fuller, N. J., Burneft, G. B. and Frane, J. W. (1988). *Endocrinology* 122: 2920–2926.
5. Zeisel, H. J., Petrykowski, W. V. and Wais, U. (1992). *Horrm. Res.* 37 (Suppl.2): 5–13.
6. Wabitsch, M. and Heinze, E. (1993). *Horrn. Res.* 49: 5–9.
7. Christman, G. M. and Halme, J. K. (1992) *Fertil. Steril.* 57:12–14.
8. Jacobs, H. S. (1992) *Horm. Res.* 38 (Suppl.1): 14–21.
9. Crist, D. M., Peake, G. T., Loftfield, R. B., Kraner, J. C. and Egan, P. A. (1991) *Mech. Ageing Dev.* 58: 191–205.
10. Strobl, J. S. and Thomas, M. J. (1994) *Pharm. Rev.* 46: 1–34.
11. Raben, M. S. and Hollenberg, C. H. (1959) *J. Clin. Invest* 38: 484–488.
12. Bengtsson, B. A., Eden, S., Lonn, L., Kvist, H., Stokland, A., Lindstedt, G., Bosaeus, I., Tolli, J., Sjostorm, L. and lsaksson, O.G.P. (1993) *J. Clin. Endocrinol Metab.* 76: 309–317.
13. Skaggs, S. R. and Crist, D. M. (1991) *Horm. Res.* 35: 19–24.
14. Etherton, T. D., Wiggins, J. P., Evock, C. M., Chung, C. S., Rebhun, J. F., Walton, P. E. and Steele, N. C. (1987). *J. Anim. Sci.* 64: 433–443.
15. Jiang, W. J., Shih, I. L., Tsai, H., Huang, Y. T. and Koh, T. J. (1993). 13th American Peptide Symposium, Edmonton, Canada, P-334 (Abstract).
16. Gertner, J. M. (1993) *Horm. Res.* 40: 10–15.
17. Davidson, M. B. (1987) *Endocrine Rev.* 8: 115–131.
18. Tai, P. K., Liao, J. F., Chen, E. H., Dietz, J., Schwards, J. and Carter-Su, C. (1990) *J. Biol. Chem.* 265: 21828–21834.
19. Dobo, M. (1975) PhD. Thesis, Department of Biochemistry, Monash University, Australia.
20. McNeillie, E. M. and Zammit, V. A. (1982) *Biochem. J.* 204: 273–288.
21. Gertner, J. M. (1992) *Horm. Res.* 38 (Suppl.2): 41–43.
22. Ng, F. M., Adamafio, N. A. and Graystone, J. E. (1990) *J. Mol. Endocnnol.* 4: 43–49.
23. Ng, F. M. and Heng, D. (1988) *Asia Pacific Commun. Biochem.* 2: 47–51.
24. Wu, Z. and Ng, F. M. (1993) *Biochem. Mol. Biol. Int.* 30: 187–96.
25. Wijaya, E. and Ng, F. M. (1993) *Biochem. Mol. Biol. Int* 31: 543–552.
26. Applied Biosystems, Inc. (1989). Peptide Synthesizer User Bulletin 29, Applied Biosystems, Inc., Foster City, Calif., USA.
27. King, D. S., Fields, C. G. and Fields, G. B. (1990) *Int. J. Peptide Protein Res.* 36: 255–266.
28. Akaji, K. A., Tatsumi, T., Yoshida, M., Kimura, T., Fujiwara, Y. and Kiso, Y. (1992) *J. Am. Chem. Soc.* 114: 4137–41–43.
29. Fossati, P., Prencipe, L. (1982) *Clin. Chem.* 28: 2077–80.
30. Allain, C. C., Poon, L. S., Chan, C. S. G., Richmond, W. and Fu, P. C. (1974) *Clin. Chem.* 20: 470–475.
31. Salem, M. A. M. and Wolff, G. L. (1989) *Proc. Soc. Exp. Biol. Med.* 191: 113–123.
32. Harris, D. M., Dunshea, F. R., Bauman, D. E., Boyd, R. D., Wang, S. Y., Johnson, P. A. and Clarke, S. D. (1993) *J. Anim. Sci.* 71: 3293–3300.
33. Folch, J., Lees, M. and Sloane-Stanley, G. H. (1957) *J. BioL Chem.* 226: 397–503.
34. Ingalls, A. M., Dickie, M. M. and Snell, G. D. (1950) *J. Hered.* 41: 317–318.
35. Thompson, J. D., Higgins, D. E. and Gibson, T. J. (1994). *Nucl. Acid. Res.* 22:4673–4680.
36. Harvey, S. et al.,"Growth Hormone", CRC Press (1995): Ascacio-Martinez et al. (1994), Gene, 143:277–280; Castro-Peretta et al. (1995), Gene, 160:311–312.

What is claimed is:

1. A method of treating obesity in a mammal, comprising administration to a mammal in need thereof an amount of a peptide, said amount being effective to reduce body weight gain and adipose tissue mass in an obese mammal, wherein (A) the amino acid sequence of said peptide comprises a carboxyl-terminal sequence of a mammalian growth hormone, selected from the group consisting of human, bovine, porcine, ovine, equine, feline, and canine growth hormones, said carboxyl-terminal sequence consisting essentially of amino acids 177 to 191 of the human growth hormone, and (B) said peptide is not the intact, full-length mammalian growth hormone.

2. The method according to claim 1, wherein said peptide does not have the diabetogenic property of the intact, full-length mammalian growth hormone.

3. The method according to claim 1, wherein the mammal is a human.

4. The method according to claim 1, wherein the amino acid sequence of said peptide comprises a carboxyl-terminal sequence of human growth hormone.

5. The method according to claim 4, wherein the amino acid sequence of said peptide comprises amino acid residues 177–191 of human growth hormone SEQ ID NO: 1.

6. The method according to claim 1, wherein the peptide is administered orally.

7. The method according to claim 1, wherein said peptide comprises as much one half of the full-length sequence of said mammalian growth hormone.

* * * * *

UNITED STATES PATENT AND TRADEMARK OFFICE
CERTIFICATE OF CORRECTION

PATENT NO. : 6,335,319 B1
DATED : January 1, 2002
INVENTOR(S) : Man-Woon NG et al.

It is certified that error appears in the above-identified patent and that said Letters Patent is hereby corrected as shown below:

Title page,
Item [73], Assignee, please change "Metabolic Pharmaceuticals, Inc., Toorak (AU)" to -- Metabolic Pharmaceuticals, Ltd., Toorak (AU) --.

Signed and Sealed this

Thirtieth Day of April, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO. : 6,335,319 B1  
DATED : January 1, 2002  
INVENTOR(S) : Man-Woon NG et al.

It is certified that error appears in the above-identified patent and that said Letters Patent is hereby corrected as shown below:

Title page,
Item [73], Assignee, please change "Metabolic Pharmaceuticals, Inc., Toorak (AU)" to -- Metabolic Pharmaceuticals, Ltd., Toorak (AU) --.

Signed and Sealed this

Thirteenth Day of August, 2002

Attest:

Attesting Officer

JAMES E. ROGAN  
Director of the United States Patent and Trademark Office

SEQUENCE LISTING

<160> NUMBER OF SEQ ID NOS: 19

<210> SEQ ID NO 1
<211> LENGTH: 15
<212> TYPE: PRT
<213> ORGANISM: Homo sapiens

<400> SEQUENCE: 1

Leu Arg Ile Val Gln Cys Arg Ser Val Glu Gly Ser Cys Gly Phe
 1               5                  10                  15

<210> SEQ ID NO 2
<211> LENGTH: 20
<212> TYPE: PRT
<213> ORGANISM: Homo sapiens

<400> SEQUENCE: 2

Lys Val Glu Thr Phe Leu Arg Ile Val Gln Cys Arg Ser Val Glu Gly
 1               5                  10                  15

Ser Cys Gly Phe
            20

<210> SEQ ID NO 3
<211> LENGTH: 26
<212> TYPE: PRT
<213> ORGANISM: Homo sapiens

<400> SEQUENCE: 3

Phe Arg Lys Asp Met Asp Lys Val Glu Thr Phe Leu Arg Ile Val Gln
 1               5                  10                  15

Cys Arg Ser Val Glu Gly Ser Cys Gly Phe
            20                  25

<210> SEQ ID NO 4
<211> LENGTH: 26
<212> TYPE: PRT
<213> ORGANISM: Homo sapiens

<400> SEQUENCE: 4

Phe Arg Lys Asp Met Asp Lys Val Glu Thr Phe Leu Arg Met Val Gln
 1               5                  10                  15

Cys Arg Ser Val Glu Gly Ser Cys Gly Phe
            20                  25

<210> SEQ ID NO 5
<211> LENGTH: 26
<212> TYPE: PRT
<213> ORGANISM: Monkey

<400> SEQUENCE: 5

Phe Arg Lys Asp Met Asp Lys Ile Glu Thr Phe Leu Arg Ile Val Gln
 1               5                  10                  15

Cys Arg Ser Val Glu Gly Ser Cys Gly Phe
            20                  25

<210> SEQ ID NO 6
<211> LENGTH: 27
<212> TYPE: PRT
<213> ORGANISM: Rattus sp.

<400> SEQUENCE: 6

```
Phe Lys Lys Asp Leu His Lys Ala Glu Thr Tyr Leu Arg Val Met Lys
 1               5                  10                  15

Cys Arg Arg Phe Ala Glu Ser Ser Cys Ala Phe
                20                  25
```

<210> SEQ ID NO 7
<211> LENGTH: 27
<212> TYPE: PRT
<213> ORGANISM: Murine

<400> SEQUENCE: 7

```
Phe Lys Lys Asp Leu His Lys Ala Glu Thr Tyr Leu Arg Val Met Lys
 1               5                  10                  15

Cys Arg Arg Phe Val Glu Ser Ser Cys Ala Phe
                20                  25
```

<210> SEQ ID NO 8
<211> LENGTH: 27
<212> TYPE: PRT
<213> ORGANISM: Hamster

<400> SEQUENCE: 8

```
Phe Lys Lys Asp Leu His Lys Ala Glu Thr Tyr Leu Arg Val Met Lys
 1               5                  10                  15

Cys Arg Arg Phe Val Glu Ser Ser Cys Ala Phe
                20                  25
```

<210> SEQ ID NO 9
<211> LENGTH: 27
<212> TYPE: PRT
<213> ORGANISM: Whale

<400> SEQUENCE: 9

```
Phe Lys Lys Asp Leu His Lys Ala Glu Thr Tyr Leu Arg Val Met Lys
 1               5                  10                  15

Cys Arg Arg Phe Val Glu Ser Ser Cys Ala Phe
                20                  25
```

<210> SEQ ID NO 10
<211> LENGTH: 27
<212> TYPE: PRT
<213> ORGANISM: Vulpes, Canis familiaris or Felis catus

<400> SEQUENCE: 10

```
Phe Lys Lys Asp Leu His Lys Ala Glu Thr Tyr Leu Arg Val Met Lys
 1               5                  10                  15

Cys Arg Arg Phe Val Glu Ser Ser Cys Ala Phe
                20                  25
```

<210> SEQ ID NO 11
<211> LENGTH: 27
<212> TYPE: PRT
<213> ORGANISM: Mustela sp.

<400> SEQUENCE: 11

```
Phe Lys Lys Asp Leu His Lys Ala Glu Thr Tyr Leu Arg Val Met Lys
 1               5                  10                  15

Cys Arg Arg Phe Val Glu Ser Ser Cys Ala Phe
                20                  25
```

<210> SEQ ID NO 12
<211> LENGTH: 27

```
<212> TYPE: PRT
<213> ORGANISM: Bos sp.

<400> SEQUENCE: 12

Phe Arg Lys Asp Leu His Lys Thr Glu Thr Tyr Leu Arg Val Met Lys
 1               5                  10                  15

Cys Arg Arg Phe Gly Glu Ala Ser Cys Ala Phe
            20                  25

<210> SEQ ID NO 13
<211> LENGTH: 27
<212> TYPE: PRT
<213> ORGANISM: Ovis sp.

<400> SEQUENCE: 13

Phe Arg Lys Asp Leu His Lys Thr Glu Thr Tyr Leu Arg Val Met Lys
 1               5                  10                  15

Cys Arg Arg Phe Gly Glu Ala Ser Cys Ala Phe
            20                  25

<210> SEQ ID NO 14
<211> LENGTH: 27
<212> TYPE: PRT
<213> ORGANISM: Capra

<400> SEQUENCE: 14

Phe Arg Lys Asp Leu His Lys Thr Glu Thr Tyr Leu Arg Val Met Lys
 1               5                  10                  15

Cys Arg Arg Phe Gly Glu Ala Ser Cys Ala Phe
            20                  25

<210> SEQ ID NO 15
<211> LENGTH: 27
<212> TYPE: PRT
<213> ORGANISM: Sus sp.

<400> SEQUENCE: 15

Phe Lys Lys Asp Leu His Lys Ala Glu Thr Tyr Leu Arg Val Met Lys
 1               5                  10                  15

Cys Arg Arg Phe Val Glu Ser Ser Cys Ala Phe
            20                  25

<210> SEQ ID NO 16
<211> LENGTH: 27
<212> TYPE: PRT
<213> ORGANISM: Lama pacos

<400> SEQUENCE: 16

Phe Lys Lys Asp Leu His Lys Ala Glu Thr Tyr Leu Arg Val Met Lys
 1               5                  10                  15

Cys Arg Arg Phe Val Glu Ser Ser Cys Ala Phe
            20                  25

<210> SEQ ID NO 17
<211> LENGTH: 27
<212> TYPE: PRT
<213> ORGANISM: Equus sp.

<400> SEQUENCE: 17

Phe Lys Lys Asp Leu His Lys Ala Glu Thr Tyr Leu Arg Val Met Lys
 1               5                  10                  15

Cys Arg Arg Phe Val Glu Ser Ser Cys Ala Phe
```

```
<210> SEQ ID NO 18
<211> LENGTH: 27
<212> TYPE: PRT
<213> ORGANISM: Elephant

<400> SEQUENCE: 18

Phe Lys Lys Asp Leu His Lys Ala Glu Thr Tyr Leu Arg Val Met Lys
 1               5                  10                  15

Cys Arg Arg Phe Val Glu Ser Ser Cys Ala Phe
            20                  25

<210> SEQ ID NO 19
<211> LENGTH: 27
<212> TYPE: PRT
<213> ORGANISM: Mammal

<400> SEQUENCE: 19

Phe Lys Lys Asp Leu His Lys Ala Glu Thr Tyr Leu Arg Val Met Lys
 1               5                  10                  15

Cys Arg Arg Phe Val Glu Ser Ser Cys Ala Phe
            20                  25
```